United States Patent [19]
Sugiyama et al.

[11] Patent Number: 6,122,049
[45] Date of Patent: Sep. 19, 2000

[54] LIQUID CHROMATOGRAPHIC APPARATUS

[75] Inventors: Yoshimi Sugiyama, Hitachinaka; Yoshiaki Yamada, Tsuchiura; Hironori Kaji; Shigeru Amiya, both of Hitachinaka, all of Japan

[73] Assignee: Hitachi, Ltd., Tokyo, Japan

[21] Appl. No.: 09/201,736

[22] Filed: Dec. 1, 1998

[30] Foreign Application Priority Data

Dec. 4, 1997 [JP] Japan .................................. 9-333960

[51] Int. Cl.$^7$ ........................................ G01N 1/10
[52] U.S. Cl. ........................................ 356/246; 356/337
[58] Field of Search ........................ 356/337–343, 356/246, 440

[56] References Cited

U.S. PATENT DOCUMENTS 4,747,687   5/1988   Hoppe et al. .
4,886,356   12/1989  Paradis .

FOREIGN PATENT DOCUMENTS 8-184551   8/1996   Japan .

*Primary Examiner*—Frank G. Font
*Assistant Examiner*—Tu T. Nguyen
*Attorney, Agent, or Firm*—Kenyon & Kenyon

[57] ABSTRACT

A flow cell is provided with a cell body having an inlet flow passage, a detection flow passage, an outlet flow passage, and windows fixed to the cell body on both sides of the detection flow passage. The inlet flow passage is formed by inserting in and closely contacting a tube in and to a hole formed in the cell body, respectively.

7 Claims, 12 Drawing Sheets

LIQUID CHROMATOGRAPHIC APPARATUS

BACKGROUND OF THE INVENTION

The present invention relates to a liquid chromatographic apparatus and particularly to a liquid chromatographic apparatus having a flow cell suitable for a micro liquid chromatography.

A conventional liquid chromatographic apparatus uses a flow cell disclosed, for example, in Japanese Patent Application Laid-Open No.8-184551 as the detector. Quartz or stainless steel having a good chemical resistance is generally used for a cell body of the flow cell. A synthetic quartz is used for windows to transmit a detection light beam and the windows are optically bonded with the cell body when the cell body is made of quartz. The cell body made of quartz is composed of an inlet flow passage, an outlet flow passage and a detection flow passage for allowing the detection light beam to pass through, the detection flow passage being connected to the inlet flow passage and the outlet flow passage. A shape of these flow passages is Z-shaped to reflect an eluant passing through the inlet flow passage by being hit on the window so that the flow separation is suppressed.

In recent yeas, processing cost of liquid waste such as organic solvents has been increased due to growing environment problems. Accordingly, it is required to reduce a using amount (flow rate) of the eluant used in the liquid chromatographic apparatus. As the flow rate of the eluant is decreased, the flow passages of the column, the flow cell and the piping are required to be made small in size in order to make diffusion of a sample small. If the sample diffuses, a peak width of chromatogram is widened, and accordingly components in the sample having peaks close to each other cannot be separated and detected.

The size of the passages of the column and the piping can be made small. However, if the diameter of the detection flow passage is decreased, a light quantity of the detection light beam is decreased and the S/N ratio is degraded. Therefore, it is necessary to reduce the diffusion of sample without decreasing the diameter of the detection flow passage. However, there are the following three problems.

1. In a flow cell of conventional structure, when the inlet flow passage is thinned in order to reduce diffusion of a sample, the inlet flow passage is easily choked by precipitation particles of the eluant and the sample. There is a problem in that if the inlet flow passage is choked, the flow cell itself has to be exchanged.

2. In a case where the cell body of a flow cell is made of quartz, the flow passages such as the inlet flow passage and the detection flow passage are formed using an ultrasonic rotary working machine. However, in boring in a quartz member using the ultrasonic rotary working machine, the minimum manufacturable diameter of the working tool is 0.4 mm, and a finishing diameter of 0.5 mm is minimum. Therefore, there is a problem in that the diameter of the inlet flow passage cannot be made smaller than the value and diffusion of sample becomes large in a quartz flow cell.

3. In a case where the diameter of the detection flow passage is not thinned in the conventional Z-shaped passage, there is a problem in that flow stagnates to increase an amount of the sample remaining at a corner portion of the detection flow passage.

SUMMARY OF THE INVENTION

An object of the present invention is to provide a liquid chromatographic apparatus comprising a flow cell which can be used without exchanging the flow cell itself when the flow passage is choked.

Another object of the present invention is to provide a liquid chromatographic apparatus comprising a flow cell which is made of quartz and has a small diameter inlet flow passage.

According to an aspect of the present invention, a liquid chromatographic apparatus is provided which comprises a column, a pump for supplying an eluant to said column so as to elute a sample to separate components thereof when said sample is introduced into said column, a flow cell through which said eluted sample flows, and a detector for detecting said separated components, wherein said flow cell comprises a cell body having an inlet flow passage, a detection flow passage and an outlet flow passage; windows fixed to said cell body on both end sides of said detection flow passage; and a tube inserted in and closely contact to a hole formed in said cell body, said inlet flow passage being formed by a hole inside said tube, and said tube being provided with an end in substantially the same plane as a trailing end of said hole formed in said cell body.

According to another aspect of the present invention, a liquid chromatographic apparatus is provided which comprises a column; a pump for supplying an eluant to said column so as to elute a sample to separate components thereof when said sample is introduced into said column; a flow cell through which said eluted sample flows; and a detector for detecting said separated components, wherein said flow cell comprises a cell body having an inlet flow passage, a detection flow passage and an outlet flow passage; windows fixed to said cell body on both end sides of said detection flow passage; and a connecting groove for branching a flow flowing out of said inlet flow passage into first and second flows and merging said first and second flows at an entrance of said detection flow passage, said connecting groove being formed in said cell body so as to connect between said inlet flow passage and said detection flow passage.

These and other objects and features of the present invention will become apparent from the descriptions of preferred embodiments of the present invention taken in connection with the accompanying drawings.

DESCRIPTION OF THE PREFERRED EMBODIMENTS

A first embodiment of a liquid chromatographic apparatus in accordance with the present invention will be described below, referring to FIG. 1 to FIG. 5.

Initially, the overall construction of an embodiment of a liquid chromatographic apparatus in accordance with the present invention will be described, referring to FIG. 1.

Figure 1:
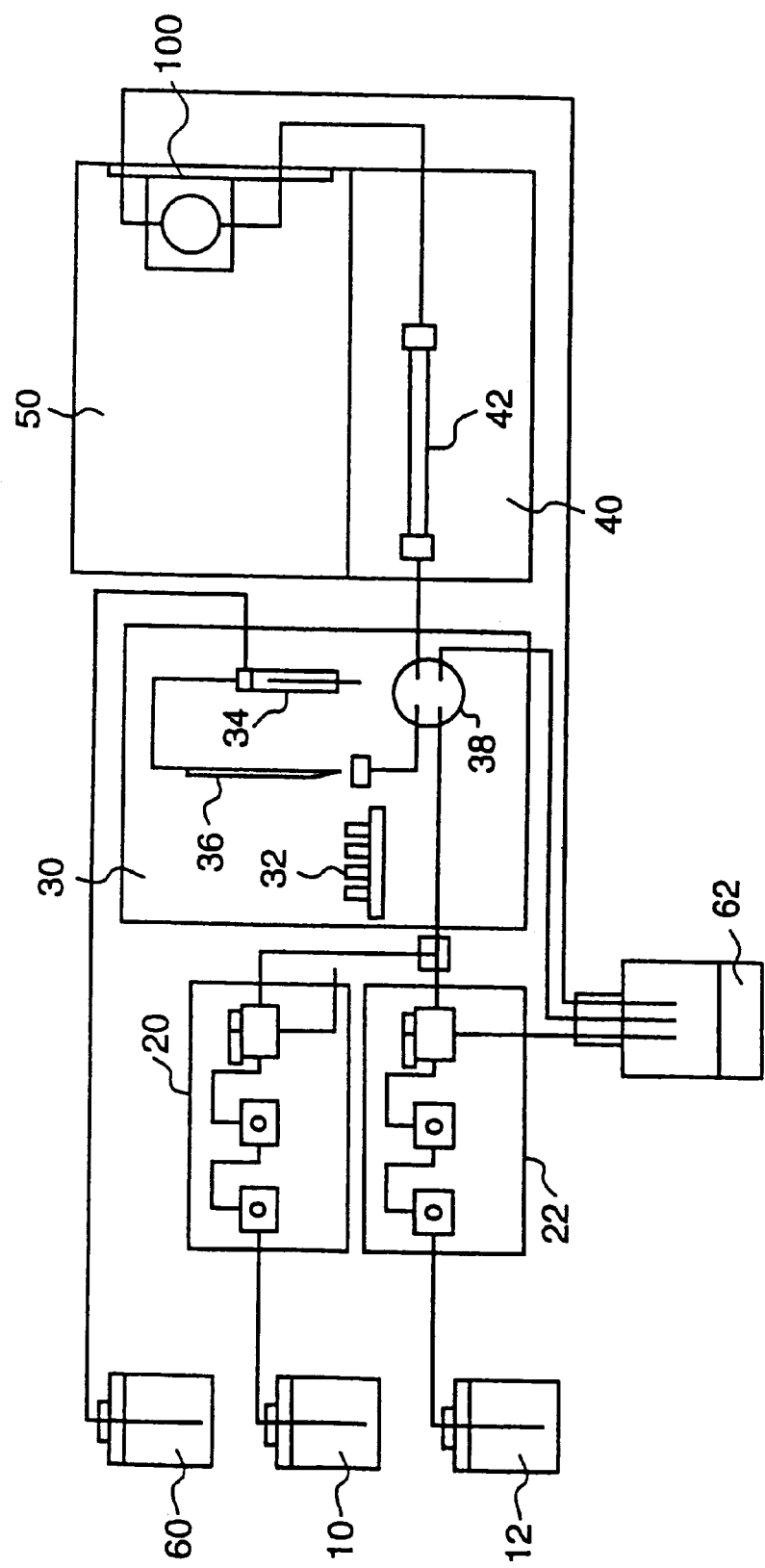
FIG. 1 is a block diagram showing the overall construction of an embodiment of a liquid chromatographic apparatus in accordance with the present invention.

FIG. 1 is a block diagram showing the overall construction of the embodiment of the liquid chromatographic apparatus in accordance with the present invention.

Eluant 10, 12 is supplied to a column 42 arranged in a column constant temperature bath 40 by pumps 20, 22 at a constant flow rate, respectively. In this embodiment, the flow rate is generally as small as 0.2 ml/minute or less. In a sample injecting unit 30, a sample 32 is introduced into a column 42 by a syringe 34 and a needle 36 through a high pressure flow path switching valve 38 so as to be eluted to separate components included of the sample 32.

In this embodiment, the column 42 generally has an inner diameter of 2 mm or less. The separated components from the column 42 are observed or detected as peaks when they flows through a flow cell 100 in a detector 50, and quantitatively measured on the basis of the height or area of the peaks.

A cleaning liquid 60 is introduced into the flow passage by a syringe 34 and a needle 36 through a high pressure flow path switching valve 38. The sample and the eluant after completion of detection are disposed to a waste liquid bottle 62.

A constitution of a flow cell of the present embodiment will be described, referring to FIG. 2 and FIG. 3.

Figure 2:
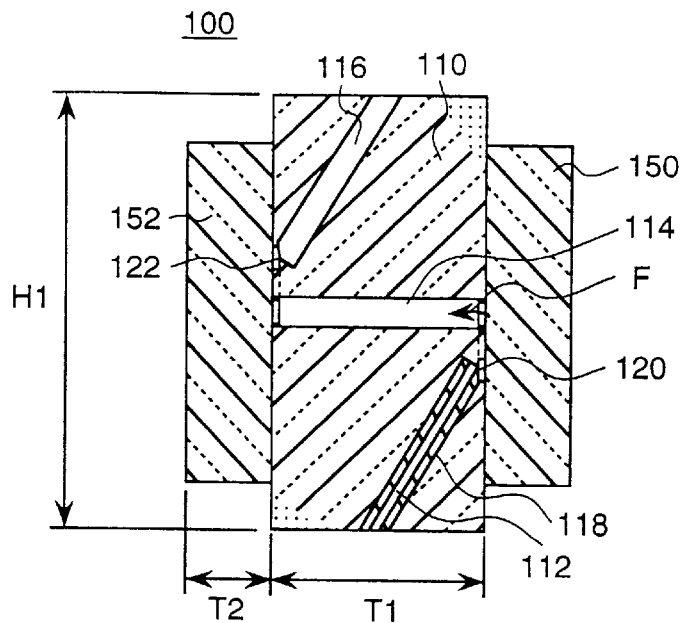
FIG. 2 is a cross-sectional view showing the cross-sectional construction of an embodiment of a flow cell used in the liquid chromatographic apparatus in accordance with the present invention.

FIG. 2 is a cross-sectional view showing the cross-sectional construction of an embodiment of a flow cell used in the liquid chromatographic apparatus in accordance with the present invention. FIG. 3 is a side view of FIG. 2 in the right hand side.

The flow cell 100 is composed of a cell body 110 and window members 150, 152. The cell body 110 is formed of an opaque black quartz. The cell body 110 is of a cylinder having two flat surfaces parallel to each other, the thickness T1 is 5 mm, the radius R1 of the circular portion is 7 mm, and the height H1 of the parallel portion is 12 mm. A transparent quartz may be used for the cell body 110, but the black quartz is preferable to reduce stray light. The thickness T2 of the window members 150, 152 is 2 mm, and the radius R2 is 5 mm. The window members 150, 152 are optically bonded to the mutually parallel end surfaces of the cell body 110.

The cell body 110 comprises an inlet flow passage 112, a detection flow passage 114 and an outlet flow passage 116 which are arranged in a Z-shape. The detection flow passage 114 and the outlet flow passage 116 are bored with a tool of an ultrasonic rotary working machine. The inner diameters of the detection flow passage 114 and the outlet flow passage 116 are 0.75 mm, respectively.

The inlet flow passage 112 is a through hole in a tube 118 which is formed by inserting the tube 118 into a hole bore-worked with a tool of the ultrasonic rotary working machine in advance. The tube 118 is made of ethylene tetra-fluoride which is excellent in chemical resistance. Another material applicable to the tube may be tri-freon or propylene which is excellent in chemical resistance and easily elastically deformable when the tube is pushed after being inserted into the hole.

The inner diameter of the hole formed by the ultrasonic rotary working machine is 0.8 mm, and the tube having an outer diameter of 0.75 mm is inserted into the hole. The leading end of the hole for forming the inlet flow passage is not completely penetrated as described later, and serves as a stopper to the leading end of the tube 118. The portion of the tube 118 extruding out of the cell body 110 is cut off. By pushing the trailing end of the tube 118 in a state that the tube 118 is inserted into the hole for forming the inlet flow passage, the tube 118 is elastically deformed, and consequently the outer surface of the tube 118 is closely attached onto the inner wall surface of the hole for forming the inlet flow passage. The inlet flow passage 112 is formed inside the tube 118, and the inner diameter becomes 0.2 mm. By the method described above, the work inserting the tube becomes stable, and the engaging allowance between the tube 118 and the hole of the cell body 110 can be loosen. Further, since the tube 118 is closely attached to the hole, movement of the tube 118 can be prevented.

That is, the minimum diameter of a hole which can be formed in a quartz cell body 110 using an ultrasonic rotary working machine is 0.5 mm, and it is impossible to form a hole having a diameter smaller than this value. However, in the present embodiment, by inserting the tube 118 into the hole formed slightly larger and closely attaching the tube to the hole, it is possible to form the inlet flow passage 112 having the inner diameter of 0.2 mm. In the past, it was impossible to form such a small diameter flow passage.

The inner diameter of the detection flow passage 114 is 0.75 mm, which is equivalent to the conventional diameter of the detection flow passage. Therefore, the quantity of detection light beam is not reduced, and accordingly the S/N ratio is not decreased. Further, since the inner diameter of the inlet flow passage 112 can be decreased as small as 0.2 mm, diffusion of the sample in the inlet flow passage can be prevented though the flow rate is decreased.

Further, since the inner diameter of the inlet flow passage 112 is 0.2 mm, the choking problem of the inlet flow passage by precipitation of the sample may occur. However, in the present embodiment, the flow cell can be reused by changing only the tube because the inlet flow passage 112 is formed by inserting the tube 118. Exchange of the tube can be easily performed by screwing a drill having a diameter slightly large than the inner diameter of the tube 118 into the inlet flow passage 112 inside the tube 118 and then pulling the drill. In the past, it was required to exchange the expensive flow cell itself. On the other hand, in the present embodiment, the exchanging cost can be reduced since only the tube is exchanged.

Furthermore, in the present embodiment, a connecting groove 120 is provided at a portion connecting the inlet flow passage 112 to the detection flow passage 114, and a connecting groove 122 is also provided at a portion connecting the detection flow passage 114 to the outlet flow passage 116. Since the shape of the connecting groove 120 is similar to the shape of connecting groove 122, the shape of the connecting groove 120 will be described here, referring to FIG. 3.

Figure 3:
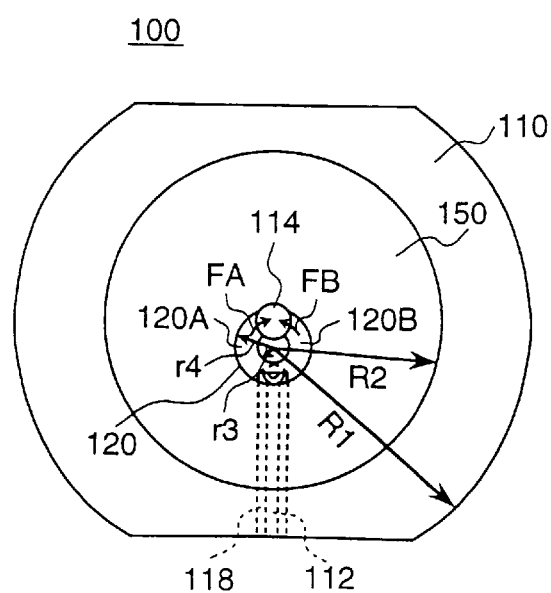
FIG. 3 is a side view of FIG. 2 in the right hand side.

As shown in FIG. 3, the connecting groove 120 is a ring-shaped groove. The inner diameter r3 of the connecting groove 120 is 0.6 mm, the outer diameter r4 is 1.6 mm, and the depth is 0.2 mm. The end portion of the inlet flow passage 112 is opened to the lower end side, in the figure, of the connecting groove 120, and the detection flow passage 114 is connected to the upper end side, in the figure, of the connecting groove 120. That is, the flow passage from the inlet flow passage 112 to the detection flow passage 114 is divided into two paths of a connecting groove 120A and a connecting groove 120B. The sample flowing into the connecting groove 120 from the end portion of the inlet flow passage 112 is branched to the connecting groove 120A and the connecting groove 120B, and then merged at the end portion of the detecting flow passage 114. At the merging portion, as shown in FIG. 3, the sample flow FA and the sample flow FB are merged, and then flow into the detection flow passage 114 as a sample flow F shown in FIG. 2. That is, since the sample flows into the detection flow passage 114 from two directions, the sample hardly stagnates. Therefore, as distinct from the conventional passage, a stagnant portion of the sample flow does not occur at the connecting portion of the inlet flow passage and the detection flow passage, and accordingly diffusion of the sample does not occur.

Since the inner diameter of the inlet flow passage 112 is 0.2 mm, the cross-sectional area is approximately 0.03 mm$^2$. On the other hand, since the inner diameter of the detection flow passage 114 is 0.75 mm, the cross-sectional area is approximately 0.44 mm$^2$. The cross-sectional shape of the connecting grooves 120A, 120B connecting the both is a rectangle 0.5 mm width and 0.2 mm depth, and the cross-sectional area is 0.1 mm$^2$. Therefore, the total cross-sectional area of the two connecting grooves 120A, 120B is 0.2 mm$^2$. That is, the cross-sectional area is gradually increased in the order of the inlet flow passage 112, the connecting groove 120 and the detection flow passage 114. Stagnation of sample is also prevented by avoiding steep change in the area of the flow passage.

Here, a tool of the ultrasonic rotary working machine for forming the connecting groove 120 will be described, referring to FIG. 4.

Figure 4:
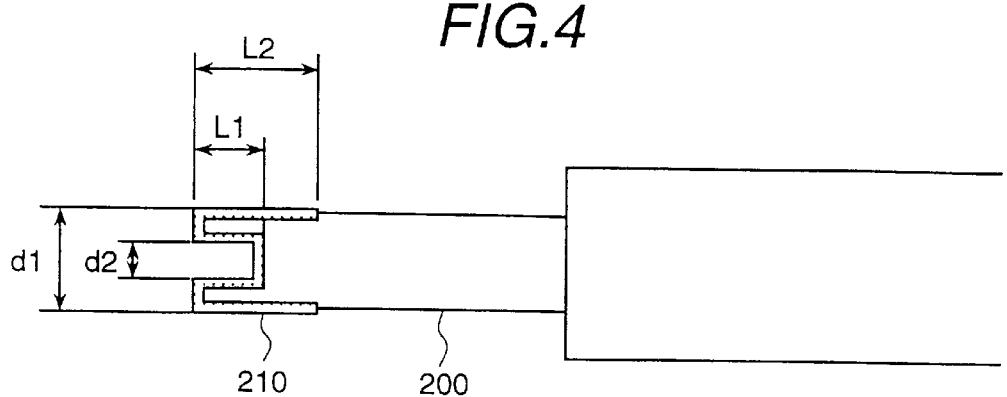
FIG. 4 is a cross-sectional view showing an ultrasonic rotary working machine for forming a connecting groove of the embodiment of the flow cell used in the liquid chromatographic apparatus in accordance with the present invention.

FIG. 4 is a cross-sectional view showing the tool of the ultrasonic rotary working machine for forming a connecting groove of the embodiment of the flow cell used in the liquid chromatographic apparatus in accordance with the present invention.

A front end of the tool 200 made of stainless steel is a ring shape having an outer diameter d1 of 1.5 mm, an inner diameter d2 of 0.7 mm and a depth L1 of 1 mm, as shown in FIG. 4. Further, diamond grinding particles 210 of # 230 grain size are electric-attached on the surface of the portion having a length L2 of 2 mm from the front end portion.

By using the tool 200, it is possible to form the connecting groove 120 having an inner diameter of 0.6 mm and an outer diameter of 1.6 mm.

Here, a chromatogram obtained by a liquid chromatographic apparatus using the flow cell of the present embodiment will be described, referring to FIG. 5.

Figure 5:
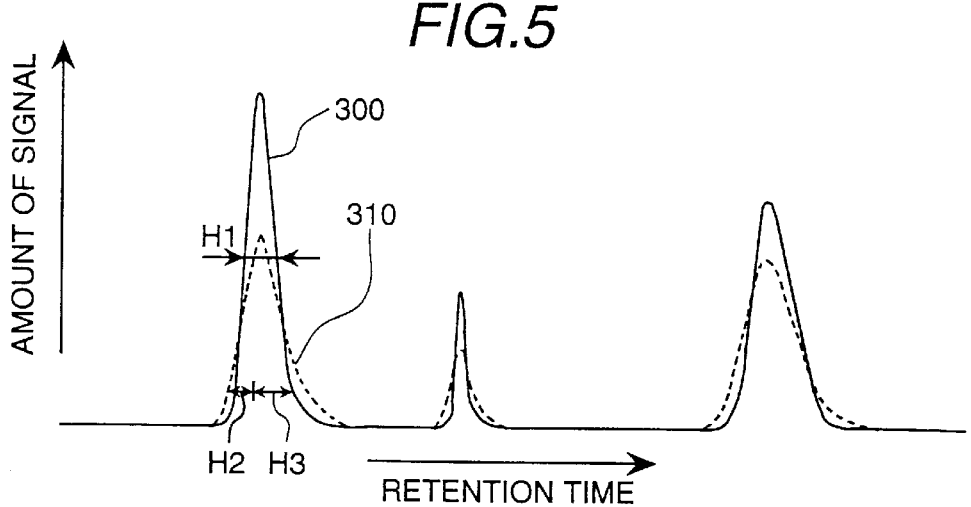
FIG. 5 is a chart explaining a chromatogram obtained by the embodiment of the liquid chromatographic apparatus in accordance with the present invention.

FIG. 5 is a chart explaining the chromatogram obtained by the embodiment of the liquid chromatographic apparatus in accordance with the present invention.

In FIG. 5, the abscissa indicates retention time, and the ordinate indicates an amount of signal. The broken line indicates a chromatogram obtained by a conventional flow cell, and the solid line indicates the chromatogram obtained by the flow cell of the present embodiment. In regard to the conventional flow cell, the inner diameter of both the inlet flow passage and the detection flow passage is 1.5 mm, and as for the measuring condition the flow rate is 1 ml/minute, and the column diameter is 4.0 mm. In regard to the present embodiment, the inner diameter of the inlet flow passage is 0.2 mm and the inner diameter of the detection flow passage is 0.75 mm, and the flow rate is 0.2 ml/minute, and the column diameter is 1.5 mm. The other measuring conditions are the same in the both flow cells.

Since the diffusion of sample is suppressed, the peak 300 for a component obtained by the present embodiment is higher and sharper than the peak 310 obtained by the conventional example. Therefore, quantitative measurement of higher separation and smaller quantity can be performed with the flow cell of the present embodiment.

The half-value width H1 in the peak 300 obtained by the present embodiment is small as compared to that of the conventional example. This is mainly because the diameter of the inlet flow passage is decreased as small as 0.2 mm.

A width H3 in the rear of the peak center at a level of 1/10 of the peak height is nearly the width H2 in the front of the peak center, that is, the symmetry of the peak is improved. This is mainly the result that occurrence of stagnation of the sample is prevented by providing the connecting groove so that the sample flows into the detection flow passage from two directions.

As described above, according to the present embodiment, since the inner diameter of the inlet flow passage can be made small by employing the tube insertion method even in a case of using the quartz cell body, it is possible to prevent diffusion of the sample in the inlet flow passage even when the rate is small.

Further, even when the inlet flow passage is choked, the flow cell can be reused by exchanging only the tube without exchanging the flow cell itself. Therefore, the exchanging cost can be reduced.

Furthermore, since stagnation of the sample hardly occurs by connecting the inlet flow passage and the detection flow passage with the connecting groove so that the sample flows into the detection flow passage from two directions, diffusion of the sample does not occur at the connecting portion of the inlet flow passage and the detection flow passage, which is different from the conventional flow cell.

Figure 6:
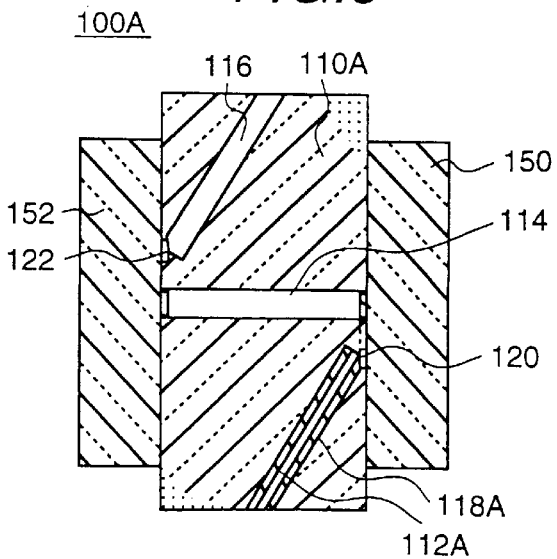
FIG. 6 is a cross-sectional view showing the cross-sectional construction of a second embodiment of a flow cell used in a liquid chromatographic apparatus in accordance with the present invention.
Figure 7:
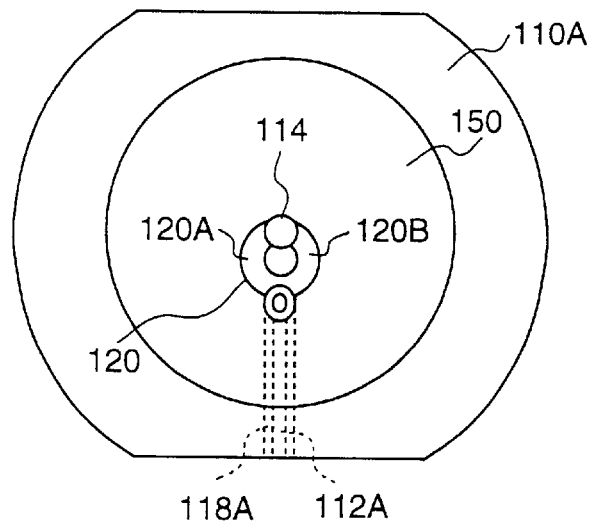
FIG. 7 is a side view of FIG. 6 in the right hand side.

A second embodiment of a liquid chromatographic apparatus in accordance with the present invention will be described, referring to FIG. 6 and FIG. 7. FIG. 6 shows the cross-sectional shape of a flow cell in accordance with the present embodiment. FIG. 7 shows the right hand side surface of FIG. 6. The overall construction of the liquid chromatographic apparatus in this embodiment is the same as that in FIG. 1. Further, in these figures, like parts are identified by the same reference characters in FIG. 2 and FIG. 3.

In this embodiment, a hole constituting the inlet flow passage is a through hole, and a tube 118A is inserted into the through hole and the window member 150 serves as a stopper for the tube 118A.

The flow cell 100A is composed of a cell body 110A made of black quartz and window members 150, 152 made of transparent quartz optically bonded to the cell body 110A. The cell body 110A comprises an inlet flow passage 112A, a detection flow passage 114 and an outlet flow passage 116 which are arranged in a Z-shape. The inlet flow passage 112A and the detection flow passage 114 are connected by the connecting groove 120, and the detection flow passage 114 and the outlet flow passage 116 are connected by the connecting groove 122.

The inlet flow passage 112A is a through hole in a tube 118A made of ethylene tetra-fluoride which is formed by inserting the tube 118A into a hole bore-worked with a tool of the ultrasonic rotary working machine in advance. Therein, the hole formed in the cell body 110A for inserting the tube 118A is a through hole. The tube 110A is inserted into the through hole, and the window member 150 is used as the stopper for the tube 118A. By pushing the trailing end of the tube 118A under a state that the tube 118A is stopped by the window member 150 after inserting the tube 118A into the through hole, the tube 118A is elastically deformed, and consequently the outer surface of the tube 118A is closely attached onto the inner wall surface of the hole for forming the inlet flow passage. Thus the inlet flow passage 112A is formed inside the tube 118A. Therein, cut portions are formed in the leading end of the tube 118A so as to communicate the inlet flow passage 112A with the connecting groove 120.

Since the hole for inserting tube 118A is the through hole, the cutting work is easier compared to cutting the hole having the stopper shown in FIG. 2.

The inner diameter of the detection flow passage 114 is 0.75 mm. Therefore, the quantity of detection light beam is not reduced, and accordingly the S/N ratio is not decreased. Further, since the inner diameter of the inlet flow passage 112A can be decreased as small as 0.2 mm, diffusion of the sample in the inlet flow passage can be prevented though the flow rate is decreased.

Further, since the inner diameter of the inlet flow passage 112A is 0.2 mm, the choking problem of the inlet flow passage 112A by precipitation of the sample may occur. However, in such an occasion, the flow cell can be reused by changing only the tube 118A.

Further, in the present embodiment, since the inlet flow passage 112A and the detection flow passage 114 are connected using the connecting groove 120, the sample hardly stagnates at the connecting portion of the inlet flow passage 112A and the detection flow passage 114. Therefore, the sample does not diffuse.

As described above, according to the present embodiment, the working to form the hole for inserting the tube becomes easier. Further, since the inner diameter of the inlet flow passage can be made small even in a case of using the quartz cell body, it is possible to prevent diffusion of the sample in the inlet flow passage even when the rate is small.

Further, even when the inlet flow passage is choked, the flow cell can be reused by exchanging only the tube without exchanging the flow cell itself. Therefore, the exchanging cost can be reduced.

Furthermore, by connecting the inlet flow passage and the detection flow passage with the connecting groove so that the sample flows into the detection flow passage from two directions, diffusion of the sample does not occur at the connecting portion of the inlet flow passage and the detection flow passage.

Figure 8:
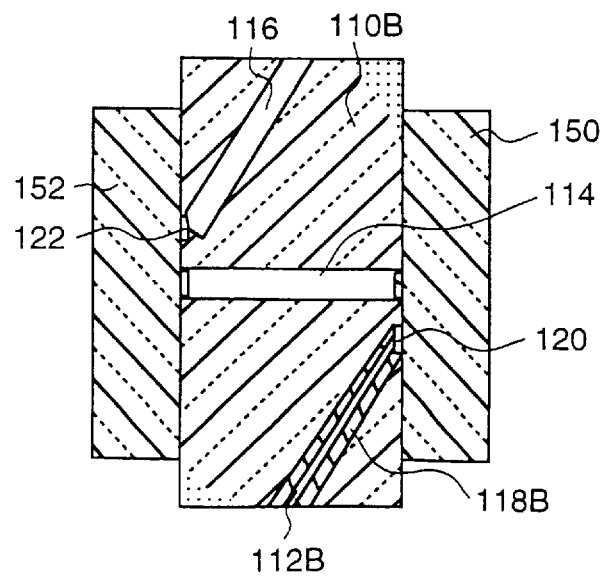
FIG. 8 is a cross-sectional view showing the cross-sectional construction of a third embodiment of a flow cell used in a liquid chromatographic apparatus in accordance with the present invention.
Figure 9:
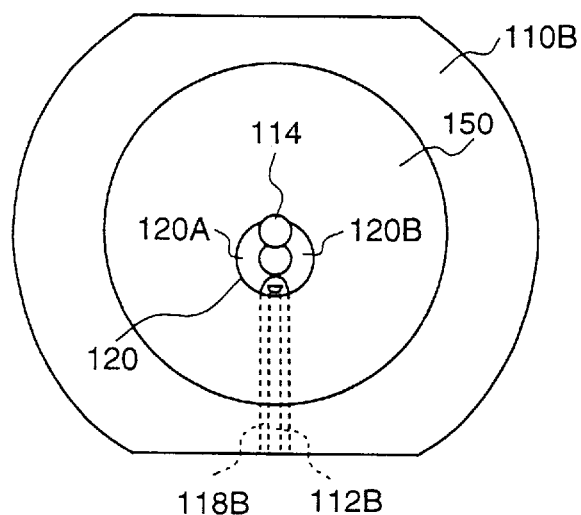
FIG. 9 is a side view of FIG. 8 in the right hand side.

A third embodiment of a liquid chromatographic apparatus in accordance with the present invention will be described, referring to FIG. 8 and FIG. 9. FIG. 8 shows the cross-sectional shape of a flow cell in accordance with the present embodiment. FIG. 9 shows the right hand side surface of FIG. 8. The overall construction of the liquid chromatographic apparatus in this embodiment is the same as that in FIG. 1. Further, in these figures, like parts are identified by the same reference characters in FIG. 2 and FIG. 3.

In this embodiment, a hole constituting the inlet flow passage is taper-shaped, and a tube 118B is inserted into the taper-shaped hole and the window member 150 in the inlet flow passage side serves as a stopper for the tube 118B.

The flow cell 100B is composed of a cell body 110B made of black quartz and window members 150, 152 made of transparent quartz optically bonded to the cell body 110B. The cell body 110B comprises an inlet flow passage 112B, a detection flow passage 114 and an outlet flow passage 116 which are arranged in a Z-shape. The inlet flow passage 112B and the detection flow passage 114 are connected by the connecting groove 120, and the detection flow passage 114 and the outlet flow passage 116 are connected by the connecting groove 122.

The inlet flow passage 112B is a through hole in a tube 118B made of ethylene tetra-fluoride which is formed by inserting the tube 118B into a hole bore-worked with a tool of the ultrasonic rotary working machine in advance.

Therein, the hole formed in the cell body 110B for inserting the tube 118B is a 1/10 tapered hole having a diameter of 0.5 mm in the side of the detection flow passage. The 1/10 tapered tube 118B having a leading end diameter 0.55 mm is inserted into the tapered through hole, and insertion of the tube 118B is stopped by engaging of the tapered portion. By pushing the trailing end of the tube 118B under a state that the tube is stopped after inserting the tube 118B into the through hole, the tube 118B is elastically deformed, and consequently the outer surface of the tube 118B is closely attached onto the inner wall surface of the hole for forming the inlet flow passage. Thus the inlet flow passage 112B is formed inside the tube 118B.

The inner diameter of the detection flow passage 114 is 0.75 mm. Therefore, the quantity of detection light beam is not reduced, and accordingly the S/N ratio is not decreased. Further, since the inner diameter of the inlet flow passage 112B can be decreased as small as 0.2 mm, diffusion of the sample in the inlet flow passage can be prevented though the flow rate is decreased.

Further, since the inner diameter of the inlet flow passage 112B is 0.2 mm, the choking problem of the inlet flow passage 112B by precipitation of the sample may occur. However, in such an occasion, the flow cell can be reused by changing only the tube 118B.

Further, in the present embodiment, since the inlet flow passage 112B and the detection flow passage 114 are connected using the connecting groove 120, the sample hardly stagnates at the connecting portion of the inlet flow passage 112B and the detection flow passage 114. Therefore, the sample does not diffuse.

As described above, according to the present embodiment, since the inner diameter of the inlet flow passage can be made small even in a case of using the quartz cell body, it is possible to prevent diffusion of the sample in the inlet flow passage even when the rate is small.

Further, even when the inlet flow passage is choked, the flow cell can be reused by exchanging only the tube without exchanging the flow cell itself. Therefore, the exchanging cost can be reduced.

Furthermore, by connecting the inlet flow passage and the detection flow passage with the connecting groove so that the sample flows into the detection flow passage from two directions, diffusion of the sample does not occur at the connecting portion of the inlet flow passage and the detection flow passage.

Figure 10:
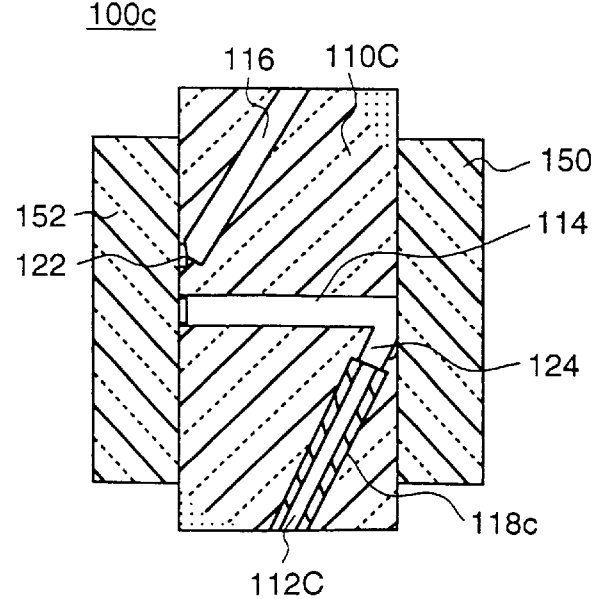
FIG. 10 is a cross-sectional view showing the cross-sectional construction of a fourth embodiment of a flow cell used in a liquid chromatographic apparatus in accordance with the present invention.

A fourth embodiment of a liquid chromatographic apparatus in accordance with the present invention will be described, referring to FIG. 10. FIG. 10 shows the cross-sectional shape of a flow cell in accordance with the present embodiment. The overall construction of the liquid chromatographic apparatus in this embodiment is the same as that in FIG. 1. Further, in these figures, like parts are identified by the same reference characters in FIG. 2.

In this embodiment, a hole for forming the inlet flow passage by inserting a tube 118C is a hole with step.

The flow cell 100C is composed of a cell body 110C made of black quartz and window members 150, 152 made of transparent quartz optically bonded to the cell body 110C. The cell body 110C comprises an inlet flow passage 112C, a detection flow passage 114 and an outlet flow passage 116 which are arranged in a Z-shape. The detection flow passage 114 and the outlet flow passage 116 are connected by the connecting groove 122. In this embodiment, the inlet flow passage 112 is directly connected to the detection flow passage 114, and the connecting groove as shown in FIG. 2 is not provided.

The inlet flow passage 112C is a through hole in a tube 118C made of ethylene tetra-fluoride which is formed by inserting the tube 118C into a hole bore-worked with a tool of the ultrasonic rotary working machine in advance. Therein, the hole formed in the cell body 110C for inserting the tube 118C is a through hole with step which has a step portion 124 at a portion in a certain depth of the through hole. By pushing the trailing end of the tube 118C under a state that the front end of the tube is stopped by the step portion 124 after inserting the tube 118C into the through hole, the tube 118C is elastically deformed, and consequently the outer surface of the tube 118C is closely attached onto the inner wall surface of the hole for forming the inlet flow passage. Thus the inlet flow passage 112C is formed inside the tube 118C.

Figure 11:
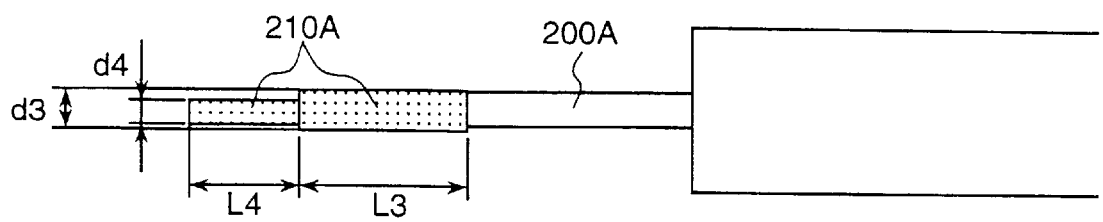
FIG. 11 is a cross-sectional view showing a tool of an ultrasonic rotary working machine for forming a hole with step in an embodiment of a flow cell used in a liquid chromatographic apparatus in accordance with the present invention.

Here, a tool of the ultrasonic rotary working machine for forming the through hole having the step portion 124 will be described, referring to FIG. 11.

The tool 200A made of stainless steel comprises a larger portion having an outer diameter d4 of 0.7 mm in front of which a smaller diameter portion having an outer diameter d3 of 0.4 mm is attached, as shown in the figure. Further, diamond grinding particles 210A of # 230 grain size are electric-attached on the surface of the larger diameter portion within a length L3 of 3 mm from the front end portion and the surface of the smaller diameter portion having a length L4 of 2 mm.

By using this tool 200A, it is possible to form the through hole with step which has an inner diameter of 0.8 mm up to a certain depth of the through hole and an inner diameter of 0.5 mm in a portion deeper than the certain depth. Therefore, the cutting work time can be reduced by using the tool with step.

The inner diameter of the detection flow passage 114 is 0.75 mm. Therefore, the quantity of detection light beam is not reduced, and accordingly the S/N ratio is not decreased. Further, since the inner diameter of the inlet flow passage 112C can be decreased as small as 0.2 mm, diffusion of the sample in the inlet flow passage can be prevented though the flow rate is decreased.

Further, since the inner diameter of the inlet flow passage 112C is 0.2 mm, the choking problem of the inlet flow passage 112C by precipitation of the sample may occur. However, in such an occasion, the flow cell can be reused by changing only the tube 118C.

As described above, according to the present embodiment, since the inner diameter of the inlet flow passage can be thinned even in a case of using the quartz cell body, it is possible to prevent diffusion of the sample in the inlet flow passage even when the rate is small.

Further, even when the inlet flow passage is choked, the flow cell can be reused by exchanging only the tube without exchanging the flow cell itself. Therefore, the exchanging cost can be reduced.

Figure 12:
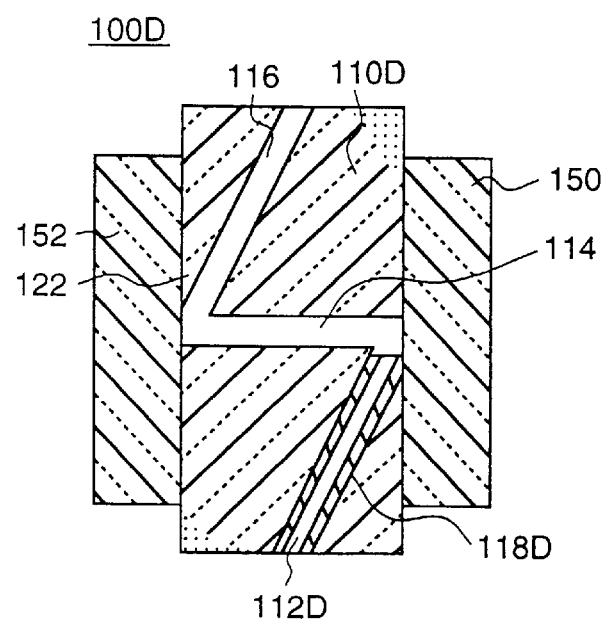
FIG. 12 is a cross-sectional view showing the cross-sectional construction of a fifth embodiment of a flow cell used in a liquid chromatographic apparatus in accordance with the present invention.

A fifth embodiment of a liquid chromatographic apparatus in accordance with the present invention will be described, referring to FIG. 12. FIG. 12 shows the cross-sectional shape of a flow cell in accordance with the present embodiment. The overall construction of the liquid chromatographic apparatus in this embodiment is the same as that in FIG. 1. Further, in these figures, like parts are identified by the same reference characters in FIG. 2.

The flow cell 100D is composed of a cell body 110D made of black quartz and window members 150, 152 made of transparent quartz optically bonded to the cell body 110D. The cell body 110D comprises an inlet flow passage 112D, a detection flow passage 114 and an outlet flow passage 116 which are arranged in a Z-shape. In this embodiment, the inlet flow passage 112D and the outlet flow passage 116 are directly connected to the detection flow passage 114, and the connecting groove as shown in FIG. 2 is not provided.

The inlet flow passage 112D is a through hole in a tube 118D made of ethylene tetra-fluoride which is formed by inserting the tube 118D into a hole bore-worked with a tool of the ultrasonic rotary working machine in advance. By pushing the trailing end of the tube 118D under a state that the front end of the tube is stopped after inserting the tube 118D into the through hole, the tube 118D is elastically deformed, and consequently the outer surface of the tube 118D is closely attached onto the inner wall surface of the hole for forming the inlet flow passage. Thus the inlet flow passage 112D is formed inside the tube 118D.

The inner diameter of the detection flow passage 114 is 0.75 mm. Therefore, the quantity of detection light beam is not reduced, and accordingly the S/N ratio is not decreased. Further, since the inner diameter of the inlet flow passage 112D can be decreased as small as 0.2 mm, diffusion of the sample in the inlet flow passage can be prevented though the flow rate is decreased.

Further, since the inner diameter of the inlet flow passage 112D is 0.2 mm, the choking problem of the inlet flow passage 112D by precipitation of the sample may occur. However, in such an occasion, the flow cell can be reused by changing only the tube 118D.

As described above, according to the present embodiment, since the inner diameter of the inlet flow passage can be thinned even in a case of using the quartz cell body, it is possible to prevent diffusion of the sample in the inlet flow passage even when the rate is small.

Further, even when the inlet flow passage is choked, the flow cell can be reused by exchanging only the tube without exchanging the flow cell itself. Therefore, the exchanging cost can be reduced.

Figure 13:
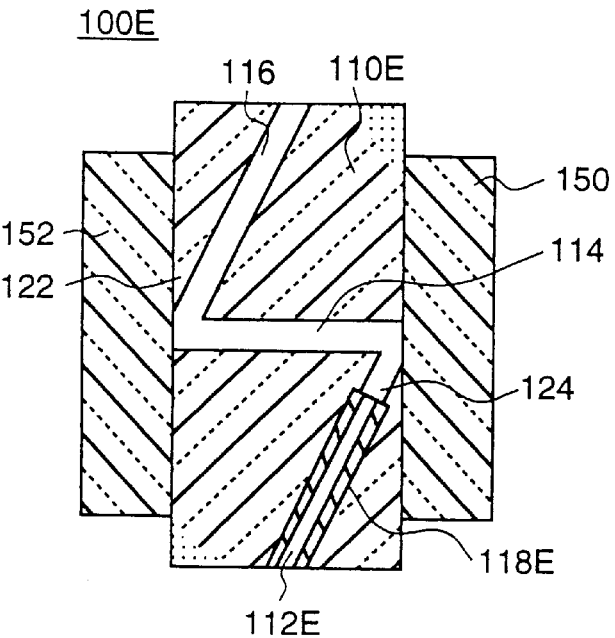
FIG. 13 is a cross-sectional view showing the cross-sectional construction of a sixth embodiment of a flow cell used in a liquid chromatographic apparatus in accordance with the present invention.

A sixth embodiment of a liquid chromatographic apparatus in accordance with the present invention will be described, referring to FIG. 13. FIG. 13 shows the cross-sectional shape of a flow cell in accordance with the present embodiment. The overall construction of the liquid chromatographic apparatus in this embodiment is the same as that in FIG. 1. Further, in these figures, like parts are identified by the same reference characters in FIG. 2.

In this embodiment, the hole for inserting a tube 118E in order to form the inlet flow passage is a hole with step.

The flow cell 100E is composed of a cell body 110E made of black quartz and window members 150, 152 made of transparent quartz optically bonded to the cell body 110E. The cell body 110E comprises an inlet flow passage 112E, a detection flow passage 114 and an outlet flow passage 116 which are arranged in a Z-shape. In this embodiment, the inlet flow passage 112E and the outlet flow passage 116 are directly connected to the detection flow passage 114, and the connecting groove as shown in FIG. 2 is not provided.

The inlet flow passage 112E is a through hole in a tube 118E made of ethylene tetra-fluoride which is formed by inserting the tube 118E into a hole bore-worked with a tool of the ultrasonic rotary working machine in advance. Therein, the hole formed in the cell body 110E for inserting the tube 118E is a through hole with step which has a step portion 124 at a portion in a certain depth of the through hole. By pushing the trailing end of the tube 118E under a state that the front end of the tube is stopped by the step portion 124 after inserting the tube 118E into the through hole, the tube 118E is elastically deformed, and consequently the outer surface of the tube 118E is closely attached onto the inner wall surface of the hole for forming the inlet flow passage. Thus the inlet flow passage 112E is formed inside the tube 118E.

The inner diameter of the detection flow passage 114 is 0.75 mm. Therefore, the quantity of detection light beam is not reduced, and accordingly the S/N ratio is not decreased. Further, since the inner diameter of the inlet flow passage 112E can be decreased as small as 0.2 mm, diffusion of the sample in the inlet flow passage can be prevented though the flow rate is decreased.

Further, since the inner diameter of the inlet flow passage 112E is 0.2 mm, the choking problem of the inlet flow passage 112E by precipitation of the sample may occur. However, in such an occasion, the flow cell can be reused by changing only the tube 118E.

As described above, according to the present embodiment, since the inner diameter of the inlet flow passage can be thinned even in a case of using the quartz cell body, it is possible to prevent diffusion of the sample in the inlet flow passage even when the rate is small.

Further, even when the inlet flow passage is choked, the flow cell can be reused by exchanging only the tube without exchanging the flow cell itself. Therefore, the exchanging cost can be reduced.

Figure 14:
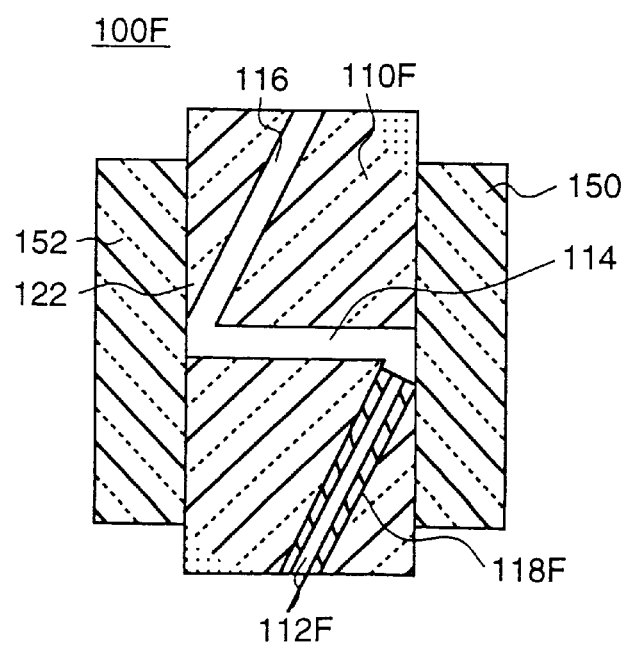
FIG. 14 is a cross-sectional view showing the cross-sectional construction of a seventh embodiment of a flow cell used in a liquid chromatographic apparatus in accordance with the present invention.

A seventh embodiment of a liquid chromatographic apparatus in accordance with the present invention will be described, referring to FIG. 14. FIG. 14 shows the cross-sectional shape of a flow cell in accordance with the present embodiment. The overall construction of the liquid chromatographic apparatus in this embodiment is the same as that in FIG. 1. Further, in these figures, like parts are identified by the same reference characters in FIG. 2.

The flow cell 100F is composed of a cell body 110F made of black quartz and window members 150, 152 made of transparent quartz optically bonded to the cell body 110F. The cell body 110F comprises an inlet flow passage 112F, a detection flow passage 114 and an outlet flow passage 116 which are arranged in a Z-shape. In this embodiment, the inlet flow passage 112F and the outlet flow passage 116 are directly connected to the detection flow passage 114, and the connecting groove as shown in FIG. 2 is not provided.

The inlet flow passage 112F is a through hole in a tube 118F made of ethylene tetra-fluoride which is formed by inserting the tube 118F into a hole bore-worked with a tool of the ultrasonic rotary working machine in advance. Therein, the hole formed in the cell body 110F for inserting the tube 118F is a 1/10 tapered hole having a diameter of 0.5 mm in the side of the detection flow passage. The 1/10 tapered tube 110B having a leading end diameter 0.55 mm is inserted into the tapered through hole, and insertion of the tube 118F is stopped by engaging of the tapered portion. By pushing the trailing end of the tube 118F under a state that the tube is stopped after inserting the tube 118F into the through hole, the tube 118F is elastically deformed, and consequently the outer surface of the tube 118F is closely attached onto the inner wall surface of the hole for forming the inlet flow passage. Thus the inlet flow passage 112F is formed inside the tube 118F.

The inner diameter of the detection flow passage 114 is 0.75 mm. Therefore, the quantity of detection light beam is not reduced, and accordingly the S/N ratio is not decreased. Further, since the inner diameter of the inlet flow passage 112F can be decreased as small as 0.2 mm, diffusion of the sample in the inlet flow passage can be prevented though the flow rate is decreased.

Further, since the inner diameter of the inlet flow passage 112F is 0.2 mm, the choking problem of the inlet flow passage 112F by precipitation of the sample may occur. However, in such an occasion, the flow cell can be reused by changing only the tube 118F.

As described above, according to the present embodiment, since the inner diameter of the inlet flow passage can be thinned even in a case of using the quartz cell body, it is possible to prevent diffusion of the sample in the inlet flow passage even when the rate is small.

Further, even when the inlet flow passage is choked, the flow cell can be reused by exchanging only the tube without exchanging the flow cell itself. Therefore, the exchanging cost can be reduced.

Figure 15:
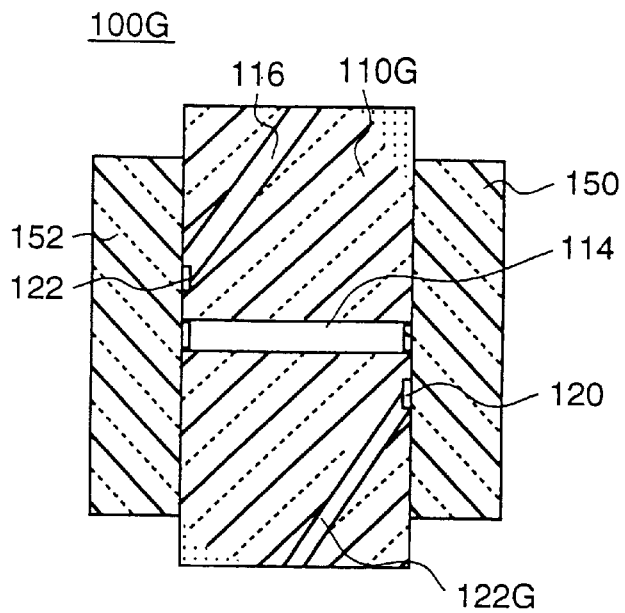
FIG. 15 is a cross-sectional view showing the cross-sectional construction of an eighth embodiment of a flow cell used in a liquid chromatographic apparatus in accordance with the present invention.
Figure 16:
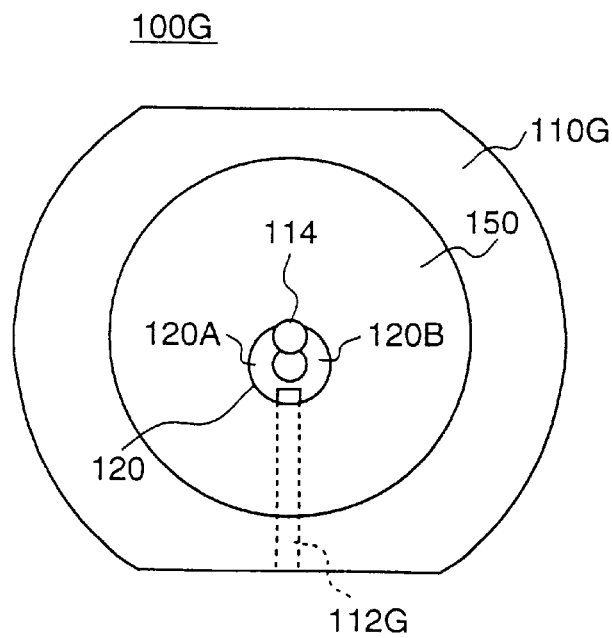
FIG. 16 is a side view of FIG. 15 in the right hand side.

An eighth embodiment of a liquid chromatographic apparatus in accordance with the present invention will be described, referring to FIG. 15 and FIG. 16. FIG. 15 shows the cross-sectional shape of a flow cell in accordance with the present embodiment. FIG. 16 shows the right hand side surface of FIG. 15. The overall construction of the liquid chromatographic apparatus in this embodiment is the same as that in FIG. 1. Further, in these figures, like parts are identified by the same reference characters in FIG. 2 and FIG. 3.

The flow cell 100G is composed of a cell body 110G made of black quartz and window members 150, 152 made of transparent quartz optically bonded to the cell body 110G. The cell body 110G comprises an inlet flow passage 112G, a detection flow passage 114 and an outlet flow passage 116 which are arranged in a Z-shape. The inlet flow passage 112G and the detection flow passage 114 are connected by the connecting groove 120, and the detection flow passage 114 and the outlet flow passage 116 are connected by the connecting groove 122.

The inlet flow passage 112G is a hole bore-worked with a tool of the ultrasonic rotary working machine in advance, and the inner diameter is 0.5 mm. The inner diameter of the detection flow passage 114 is 0.75 mm. Therefore, the quantity of detection light beam is not reduced, and accordingly the S/N ratio is not decreased.

Further, in the present embodiment, since the inlet flow passage 112G and the detection flow passage 114 are connected using the connecting groove 120, the sample hardly stagnates at the connecting portion of the inlet flow passage 112G and the detection flow passage 114. Therefore, the sample does not diffuse.

As described above, according to the present embodiment, by connecting the inlet flow passage and the detection flow passage with the connecting groove so that the sample flows into the detection flow passage from two directions, diffusion of the sample does not occur at the connecting portion of the inlet flow passage and the detection flow passage.

Figure 17:
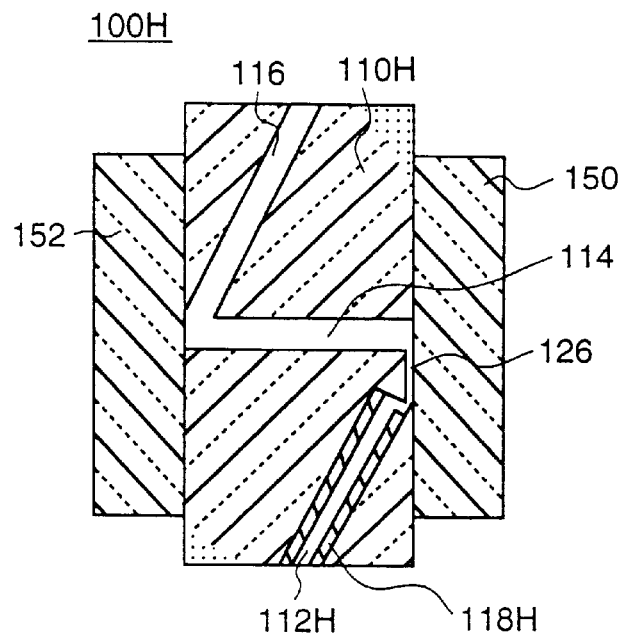
FIG. 17 is a cross-sectional view showing the cross-sectional construction of a fifth embodiment of a flow cell used in a liquid chromatographic apparatus in accordance with the present invention.

A ninth embodiment of a liquid chromatographic apparatus in accordance with the present invention will be described, referring to FIG. 17. FIG. 17 shows the cross-sectional shape of a flow cell in accordance with the present embodiment. The overall construction of the liquid chromatographic apparatus in this embodiment is the same as that in FIG. 1. Further, in these figures, like parts are identified by the same reference characters in FIG. 2 and FIG. 3.

The flow cell 100H is composed of a cell body 110H made of black quartz and window members 150, 152 made of transparent quartz optically bonded to the cell body 110H. The cell body 110H comprises an inlet flow passage 112H, a detection flow passage 114 and an outlet flow passage 116 which are arranged in a Z-shape. The inlet flow passage 112H and the detection flow passage 114 are connected by a belt-shaped connecting flow passage 126.

The inlet flow passage 112H is a through hole in a tube 118H made of ethylene tetra-fluoride which is formed by inserting the tube 118H into a hole bore-worked with a tool of the ultrasonic rotary working machine in advance. Therein, the front end of the hole formed in the cell body 110H for inserting the tube 118E is not completely penetrated, but formed as a stopper to the front end of the tube 118H. By pushing the trailing end of the tube 118H after inserting the tube 118H into the hole for forming the inlet flow passage, the tube 118H is elastically deformed, and consequently the outer surface of the tube 118H is closely attached onto the inner wall surface of the hole for forming the inlet flow passage. Thus the inlet flow passage 112H is formed inside the tube 118H.

The inner diameter of the detection flow passage 114 is 0.75 mm. Therefore, the quantity of detection light beam is not reduced, and accordingly the S/N ratio is not decreased. Further, since the inner diameter of the inlet flow passage 112H can be decreased as small as 0.2 mm, diffusion of the sample in the inlet flow passage can be prevented though the flow rate is decreased.

Further, since the inner diameter of the inlet flow passage 112H is 0.2 mm, the choking problem of the inlet flow passage 112H by precipitation of the sample may occur. However, in such an occasion, the flow cell can be reused by changing only the tube 118H.

As described above, according to the present embodiment, it is easy to form the hole for inserting the tube, and it is possible to prevent diffusion of the sample in the inlet flow passage even when the rate is small since the inner diameter of the inlet flow passage can be thinned even in a case of using the quartz cell body.

Further, even when the inlet flow passage is choked, the flow cell can be reused by exchanging only the tube without exchanging the flow cell itself. Therefore, the exchanging cost can be reduced.

Figure 18:
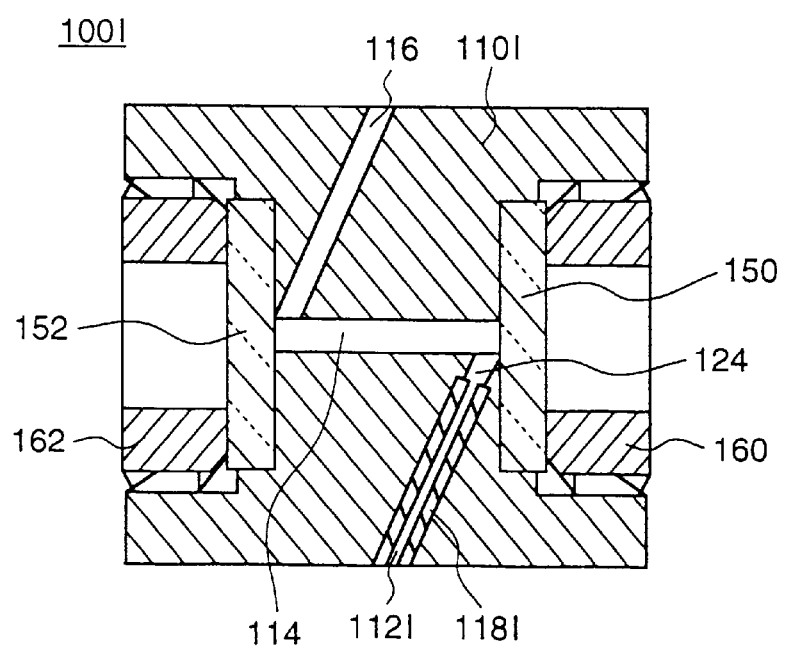
FIG. 18 is a cross-sectional view showing the cross-sectional construction of a tenth embodiment of a flow cell used in a liquid chromatographic apparatus in accordance with the present invention.

A tenth embodiment of a liquid chromatographic apparatus in accordance with the present invention will be described, referring to FIG. 18. FIG. 18 shows the cross-sectional shape of a flow cell in accordance with the present embodiment. The overall construction of the liquid chromatographic apparatus in this embodiment is the same as that in FIG. 1. Further, in these figures, like parts are identified by the same reference characters in FIG. 2.

In this embodiment, the cell body 110I is made of stainless steel, and the hole for forming the inlet flow passage by inserting a tube 118I is a hole with step.

The flow cell 100I is composed of a cell body 110I made of stainless steel and window members 150, 152 made of transparent quartz fixed to the cell body 110I by window holders 160, 162. The cell body 110I comprises an inlet flow passage 112I, a detection flow passage 114 and an outlet flow passage 116 which are arranged in a Z-shape. In this embodiment, the inlet flow passage 112I and the outlet flow passage 116 are directly connected to the detection flow passage 114.

The inlet flow passage 112I is a through hole in a tube 118I made of ethylene tetra-fluoride which is formed by inserting the tube 118I into a hole bore-worked with a drill. Therein, the hole formed in the cell body 110I for inserting the tube 118I is a through hole with step which has a step portion 124 at a portion in a certain depth of the through hole. By pushing the trailing end of the tube 118I under a state that the front end of the tube is stopped by the step portion 124 to enter further after inserting the tube 118I into the through hole, the tube 118I is elastically deformed, and consequently the outer surface of the tube 118I is closely attached onto the inner wall surface of the hole for forming the inlet flow passage. Thus the inlet flow passage 112I is formed inside the tube 118I.

The inner diameter of the detection flow passage 114 is 0.75 mm. Therefore, the quantity of detection light beam is not reduced, and accordingly the S/N ratio is not decreased. Further, since the inner diameter of the inlet flow passage 112I can be decreased as small as 0.2 mm, diffusion of the sample in the inlet flow passage can be prevented though the flow rate is decreased.

Further, since the inner diameter of the inlet flow passage 112I is 0.2 mm, the choking problem of the inlet flow passage 112I by precipitation of the sample may occur. However, in such an occasion, the flow cell can be reused by changing only the tube 118I.

As described above, according to the present embodiment, even when the inlet flow passage is choked, the flow cell can be reused by exchanging only the tube without exchanging the flow cell itself. Therefore, the exchanging cost can be reduced.

Figure 19:
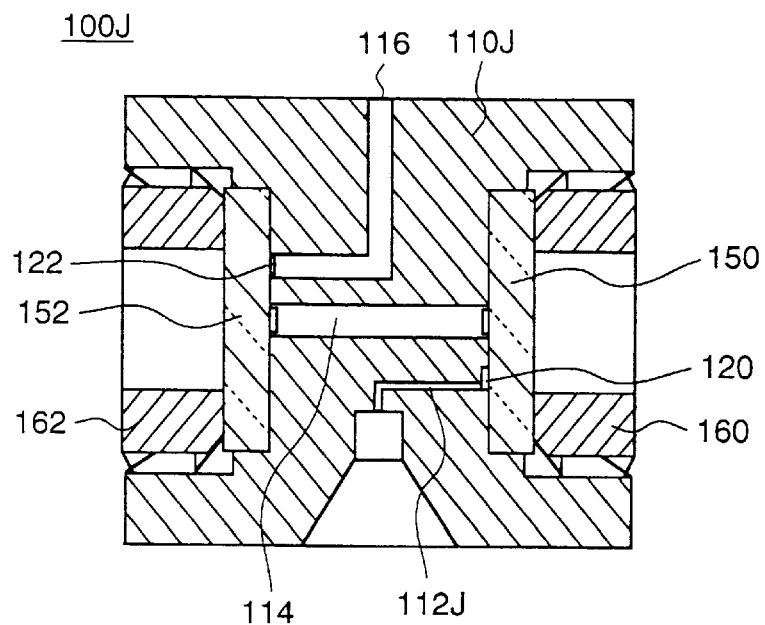
FIG. 19 is a cross-sectional view showing the cross-sectional construction of an eleventh embodiment of a flow cell used in a liquid chromatographic apparatus in accordance with the present invention.
Figure 20:
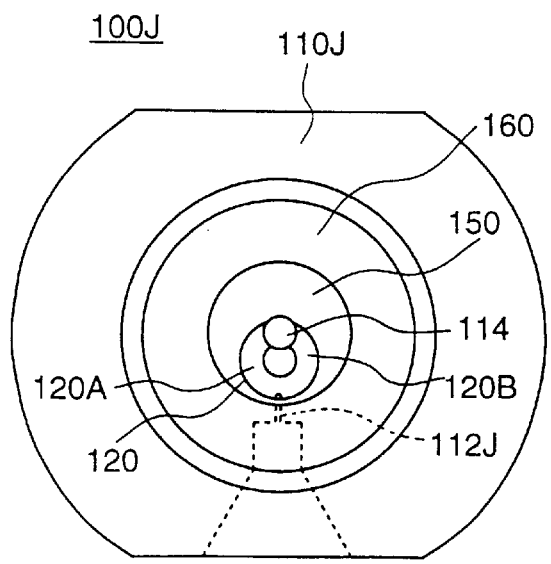
FIG. 20 is a side view of FIG. 19 in the right hand side.

An eleventh embodiment of a liquid chromatographic apparatus in accordance with the present invention will be described, referring to FIG. 19 and FIG. 20. FIG. 19 shows the cross-sectional shape of a flow cell in accordance with the present embodiment. FIG. 20 shows the right hand side surface of FIG. 19. The overall construction of the liquid chromatographic apparatus in this embodiment is the same as that in FIG. 1. Further, in these figures, like parts are identified by the same reference characters in FIG. 2 and FIG. 3.

The flow cell 100J is composed of a cell body 110J made of stainless steel and window members 150, 152 made of transparent quartz fixed to the cell body 110J by window holders 160, 162. The cell body 110J comprises an inlet flow passage 112J, a detection flow passage 114 and an outlet flow passage 116 which are arranged in a Z-shape. The inlet flow passage 112J and the detection flow passage 114 are connected by a connecting groove 120, and the detection flow passage 114 and the outlet flow passage 116 are connected by a connecting groove 122.

The inner diameter of the detection flow passage 114 is 0.75 mm. Therefore, the quantity of detection light beam is not reduced, and accordingly the S/N ratio is not decreased. Further, since the inner diameter of the inlet flow passage 112J can be decreased as small as 0.2 mm, diffusion of the sample in the inlet flow passage can be prevented though the flow rate is decreased.

Further, in the present embodiment, by connecting the inlet flow passage 112J and the detection flow passage 114 with the connecting groove 120, stagnation of the sample hardly occurs and diffusion of the sample does not occur at the connecting portion of the inlet flow passage 112J and the detection flow passage 114.

As described above, according to the present embodiment, it is easy to form the hole for inserting the tube, and it is possible to prevent diffusion of the sample in the inlet flow passage even when the rate is small since the inner diameter of the inlet flow passage can be thinned even in a case of using the stainless steel cell body.

Further, by connecting the inlet flow passage and the detection flow passage with the connecting groove so that the sample flows into the detection flow passage from two directions, diffusion of the sample does not occur at the connecting portion of the inlet flow passage and the detection flow passage.

Figure 21:
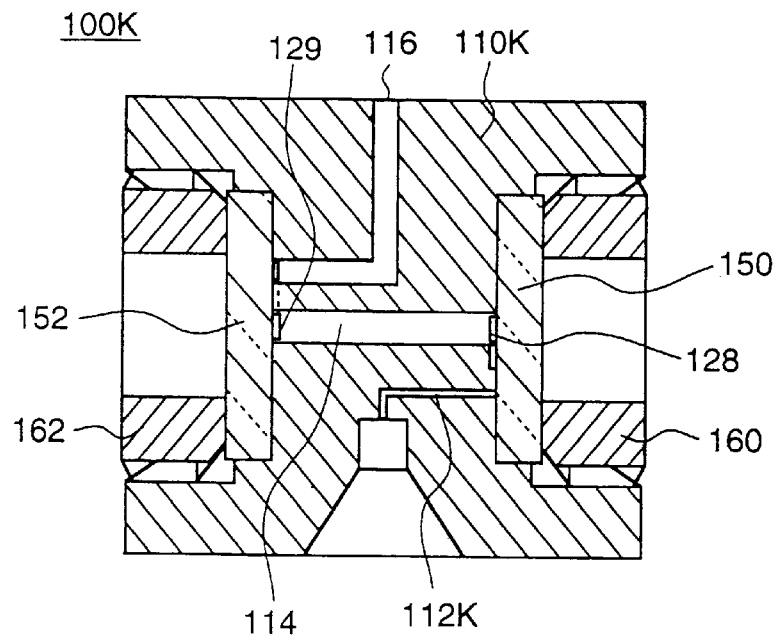
FIG. 21 is a cross-sectional view showing the cross-sectional construction of a twelfth embodiment of a flow cell used in a liquid chromatographic apparatus in accordance with, the present invention.
Figure 22:
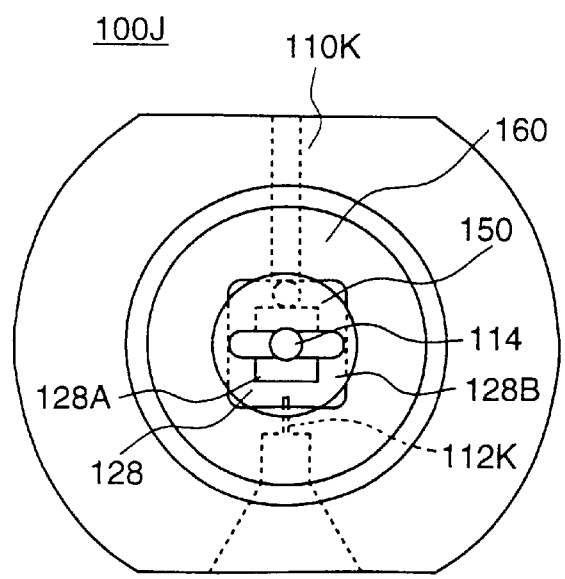
FIG. 22 is a side view of FIG. 21 in the right hand side.

A twelfth embodiment of a liquid chromatographic apparatus in accordance with the present invention will be described, referring to FIG. 21 and FIG. 22. FIG. 21 shows the cross-sectional shape of a flow cell in accordance with the present embodiment. FIG. 22 shows the right hand side surface of FIG. 21. The overall construction of the liquid chromatographic apparatus in this embodiment is the same as that in FIG. 1. Further, in these figures, like parts are identified by the same reference characters in FIG. 2 and FIG. 3.

The flow cell 100K is composed of a cell body 110K made of stainless steel and window members 150, 152 made of transparent quartz fixed to the cell body 110K by window holders 160, 162. The cell body 110K comprises an inlet flow passage 112K, a detection flow passage 114 and an outlet flow passage 116 which are arranged in a Z-shape. The inlet flow passage 112K and the detection flow passage 114 are connected by a connecting groove 128, and the detection flow passage 114 and the outlet flow passage 116 are connected by a connecting groove 129. The connecting groove 128 and the connecting groove 129 are the same shape.

As shown in FIG. 22, the connecting groove 128 is a rectangular ring-shape. The end portion of the inlet flow passage 112K is opened to the lower end side, in the figure, of the connecting groove 128, and the detection flow passage 114 is connected to the upper end side, in the figure, of the connecting groove 128. That is, the flow passage from the inlet flow passage 112K to the detection flow passage 114 is divided into two paths of a connecting groove 128A and a connecting groove 128B. The sample flowing into the connecting groove 128 from the end portion of the inlet flow passage 112K is branched to the connecting groove 128A and the connecting groove 128B, and then merged at the end portion of the detecting flow passage 114. At the merging portion, the two sample flows are merged, and then flow into the detection flow passage 114. That is, since the sample flows into the detection flow passage 114 from two directions, the sample hardly stagnates. Therefore, different from the conventional passage, a stagnant portion of the sample flow does not occur at the connecting portion of the inlet flow passage and the detection flow passage, and accordingly diffusion of the sample does not occur.

The inner diameter of the detection flow passage 114 is 0.75 mm. Therefore, the quantity of detection light beam is not reduced, and accordingly the S/N ratio is not decreased. Further, since the inner diameter of the inlet flow passage 112K can be decreased as small as 0.2 mm, diffusion of the sample in the inlet flow passage can be prevented though the flow rate is decreased.

Further, in the present embodiment, by connecting the inlet flow passage 112K and the detection flow passage 114 with the connecting groove 120, stagnation of the sample hardly occurs and diffusion of the sample does not occur at the connecting portion of the inlet flow passage 112K and the detection flow passage 114.

As described above, according to the present embodiment, it is easy to form the hole for inserting the tube, and it is possible to prevent diffusion of the sample in the inlet flow passage even when the rate is small since the inner diameter of the inlet flow passage can be thinned even in a case of using the stainless steel cell body.

Further, by connecting the inlet flow passage and the detection flow passage with the connecting groove so that the sample flows into the detection flow passage from two directions, diffusion of the sample does not occur at the connecting portion of the inlet flow passage and the detection flow passage.

As having been described above, according to each of the embodiments of the present invention, 1) by press fitting the tube into the inlet flow passage, the volume of the inlet flow passage can be reduced as compared to that of the inlet flow passage in the conventional quartz flow cell; 2) by press fitting the tube into the inlet flow passage, the tube can be easily repaired by exchanging the tube when the inlet flow passage is choked; 3) by employing ethylene tetra-fluoride as the material for the tube to be press-fit into the inlet flow passage, choking of the inlet flow passage by precipitating particles can be prevented; 4) by arranging a plurality of flow grooves connecting between the inlet and the outlet flow passages with the detection flow passage, flow stagnant portions are decreased and accordingly diffusion of the sample in the detection flow passage can be reduced; 5) by forming the flow groove connecting the inlet and the outlet flow passage with the detection flow passage in a ring shape, cost of working using the ultrasonic rotary working machine can be reduced; and 6) the S/N ratio of detection signal can be increased and noise in the chromatogram can be reduced since light amount of detection light beam is large compared to that in a flow cell having a small diameter detection flow passage in order to reduce diffusion of a sample.

Figure 23:
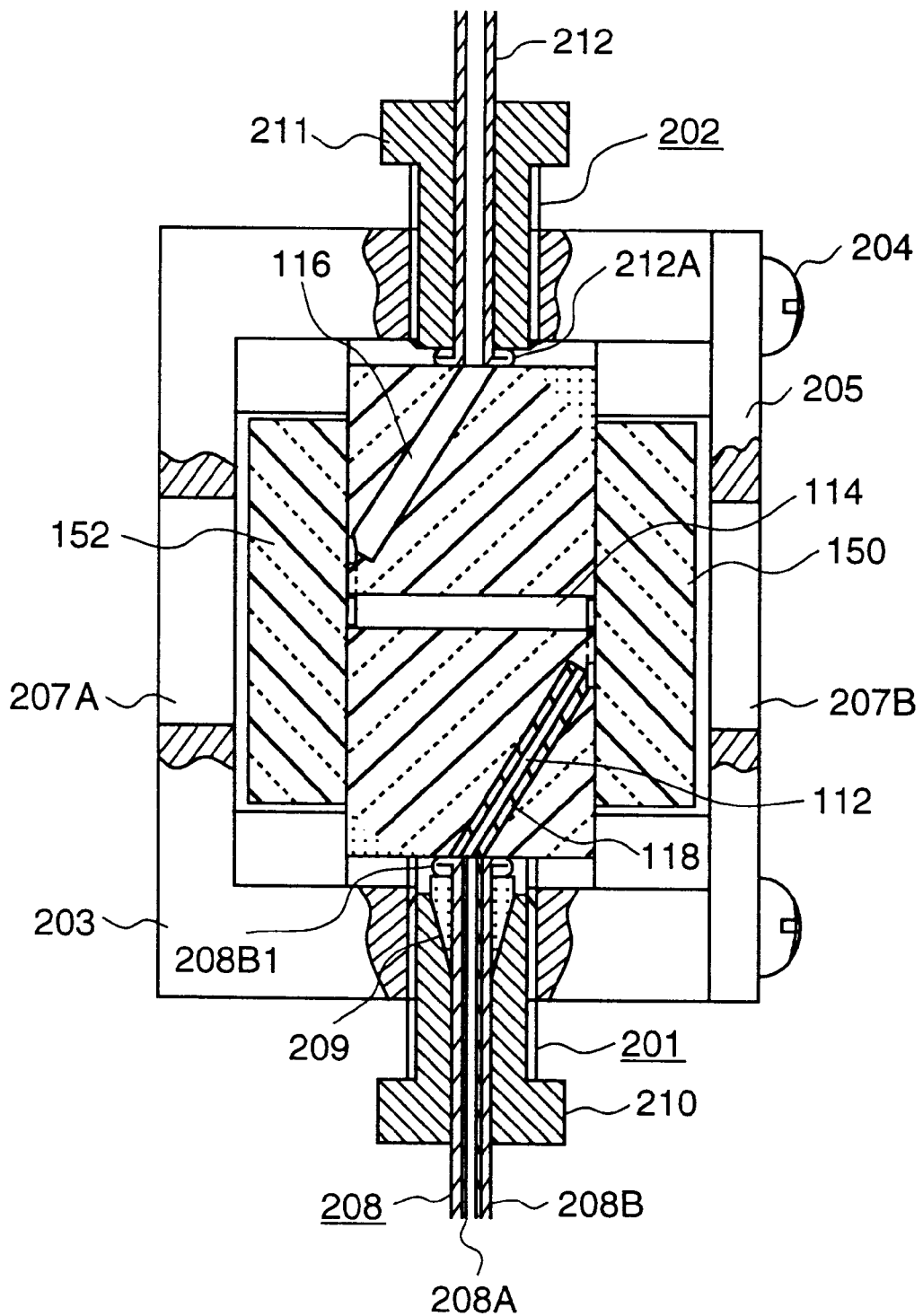
FIG. 23 is a view showing an embodiment of a flow cell assembly used in a liquid chromatographic apparatus in accordance with the present invention.

FIG. 23 shows an embodiment of a flow cell assembly used in a liquid chromatographic apparatus in accordance with the present invention. The flow cell assembly comprises a cell holder 200; a flow cell 100 arranged in the cell holder; a fixing unit 201 for fixing the flow cell 100 to the cell holder 200 and for stably connecting a double tube 208 to be described later to the tube 118; and a fixing unit 202 for fixing the flow cell 100 to the cell holder 200 and for connecting a tube 212 to be described later to the outlet flow passage 116. The flow cell 100 may be any one of the flow cells of the first to the tenth embodiments, but the flow cell of the first embodiment shown in FIG. 2 is employed in the figure for convenience sake.

The cell holder 200 is composed of a cell holder main body 203 and a cell holder cover 205 fixed to the cell holder main body 203 with screws 204, and the cell holder main body 203 and the cell holder cover 205 have light pass holes 207A and 207B opposite to the window members 152 and 150, respectively.

The double tube 208 is composed of an inner tube 208A made of stainless steel of 0.1 mm inner diameter and 0.5 mm outer diameter; and an outer tube 208B made of polytetrafluoroethyl (PTFE) of 0.5 mm inner diameter and 1.3 mm outer diameter covering the inner tube. The outer tube 208B has at the end thereof a flange portion 208B1 extending in the radial direction.

The fixing unit 201 is composed of a sleeve 209 made of PTFE which is fit on the outer periphery of the leading end of the outer tube 208, and has a taper expanding toward the flow cell 100 side on the outside surface; and a pushing screw 210 which is engaged with the cell holder main body 203, and has a hole for penetrating the double tube 208 on the inside surface and a taper for engaging with the sleeve 208 on the outside surface.

A portion of the tube 118 of the flow cell 100 is extruded from the cell body 110 when the tube is inserted into the hole forming the inlet flow passage 112. The extruded portion of the tube 118 is cut off with a sharp cutter. The inlet end of the remaining tube 118 by the cutting, that is, the trailing end or upstream end of the tube 118 is in a substantially even level or plane with the bottom end surface of the cell body 110, that is, the inlet side end (trailing end) of the hole forming the inlet flow passage 112.

By screwing the pushing screw 210 to move it toward the inside of the cell holder 200, the sleeve 209 pushes the outer tube 208B and the flange portion 208B1 of the end of the outer tube 208B because of engagement between the taper of the pushing screw 210 and the taper of the sleeve 209. Thereby, the flange portion 208B1 is pushed to the end surfaces of the cell body 110 and the tube 118 on the inlet side thereof together with the inner tube 208A. Therefore, the inner tube 208A is communicated to the tube 118, with the tube 118 deformed elastically, and consequently the liquid introduced in the inner tube 208 is conducted to the tube 118 without leakage.

The fixing unit 202 comprises a pushing screw 211 screwed to the cell body 200. By screwing the pushing screw 211 to move it downward, the bottom end of the pushing screw 211 pushes a flange portion 212A in the lower end of a tube 212 made of PTFE. Thereby, the tube 212 and the outlet flow passage 116 are stably connected to each other.

According to the present invention, a flow cell used in a liquid chromatographic apparatus can be reused without exchanging the flow cell itself when the flow cell is choked.

Further, according to the present invention, the diameter of an inlet flow passage in a quartz flow cell used in a liquid chromatographic apparatus can be made small.

Further, according to the present invention, an amount of remaining sample can be reduced with out decreasing the diameter of an inlet flow passage in a quartz flow cell used in a liquid chromatographic apparatus.

Since it is obvious that many changes and modifications can be made in the above described details without departing from the nature and spirit of the present invention, it is to be understood that the present invention is not to be limited to the details described herein.

What is claimed is:

1. A liquid chromatographic apparatus comprising a column; a pump for supplying an eluant to said column so as to elute a sample to separate components thereof when said sample is introduced into said column; a flow cell through which said eluted sample flows; and a detector for detecting said separated components, wherein said flow cell comprises:
a cell body having an inlet flow passage, a detection flow passage connected to said inlet flow passage and an outlet flow passage connected to said detection flow passage;
windows fixed to said cell body on both end sides of said detection flow passage; and
a tube inserted in and closely contact to a hole formed in said cell body, said inlet flow passage being formed in said cell body, said inlet flow passage being formed by a hole inside said tube, and said tube being provided with a trailing end in substantially the same plane as a trailing end of said hole formed in said cell body.

2. A liquid chromatographic apparatus according to claim 1, wherein said cell body is made of quartz.

3. A liquid chromatographic apparatus according to claim 1, wherein said hole formed in said cell body is of a taper-shape, and an outer shape of said tube is of a taper-shape.

4. A liquid chromatographic apparatus according to claim 1, wherein said hole formed in said cell body is provide with a step portion at a leading end thereof, and a trailing end of said tube is engaged with said step portion.

5. A liquid chromatographic apparatus according to claim 1, wherein said tube is formed of a material which is chemical resistant and elastically deformable.

6. A liquid chromatographic apparatus comprising a column; a pump for supplying an eluant to said column so as to elute a sample to separate components thereof when said sample is introduced into said column; a flow cell through which said eluted sample flows; and a detector for detecting said separated components, wherein said flow cell comprises:
 a cell body having an inlet flow passage, a detection flow passage and an outlet flow passage;
 windows fixed to said cell body on both end sides of said detection flow passage; and
 a connecting groove for branching a flow flowing out of said inlet flow passage into first and second flows and merging said first and second flows at an entrance of said detection flow passage, said connecting groove being formed in said cell body so as to connect between said inlet flow passage and said detection flow passage.

7. A liquid chromatographic apparatus according to claim 6, wherein said connecting groove is formed in a ring shape in said cell body, said inlet flow passage being connected to a part of said ring-shaped connecting groove, said detection flow passage being connected to said ring-shaped connecting groove at a position substantially symmetrical with respect to the connecting portion of said inlet flow passage and said connecting groove.

* * * * *